United States Patent [19]

Sakakibara et al.

[11] 4,052,462

[45] Oct. 4, 1977

[54] CATALYST COMPOSITION FOR OXIDATION OF OLEFINS

[75] Inventors: Kouzou Sakakibara; Iwao Abe; Takushi Yokoyama; Kazuyuki Matuokadeclare, all of Saitama, Japan

[73] Assignee: Daicel Ltd., Osaka, Japan

[21] Appl. No.: 632,358

[22] Filed: Nov. 17, 1975

Related U.S. Application Data

[63] Continuation of Ser. No. 363,521, May 24, 1973, abandoned.

[30] Foreign Application Priority Data

June 9, 1972 Japan .................................. 47-57421

[51] Int. Cl.$^2$ ............................................. C07C 45/16
[52] U.S. Cl. .................................................. 260/604 R
[58] Field of Search ............................ 252/456, 469; 260/604 R, 603 R, 603 C

[56] References Cited

U.S. PATENT DOCUMENTS

| 2,941,007 | 6/1960 | Callahan et al. ................ 260/604 R |
| 3,522,299 | 7/1970 | Takenaka ........................ 260/604 R |

FOREIGN PATENT DOCUMENTS 906,215  8/1972  United Kingdom ................ 260/604

Primary Examiner—James O. Thomas, Jr.
Assistant Examiner—W. B. Lone
Attorney, Agent, or Firm—Blanchard, Flynn, Thiel, Boutell & Tanis

[57] ABSTRACT

A catalyst cmposition for the gas phase oxidation of $\alpha,\beta$-unsaturated olefinic hydrocarbons comprising at least two metal oxides, at least one of which contains molybdenum, and a silica carrier having a specific surface area of at least 250 m$^2$/g, the catalyst composition as a whole having a specific surface area of from 100 to 250 m$^2$/g.

7 Claims, 2 Drawing Figures

| | CATALYST | REACTION TEMP. |
|---|---|---|
| A | EXAMPLE 1 | 340°C |
| B | COMPARATIVE EXAMPLE 1 | 340°C |
| C | EXAMPLE 1 | 360°C |

| | CATALYST | REACTION TEMP. |
|---|---|---|
| D | EXAMPLE 3 | 355°C |
| E | EXAMPLE 3 | 385°C |
| F | COMPARATIVE EXAMPLE 2 | 385°C |

CATALYST COMPOSITION FOR OXIDATION OF OLEFINS

This is a continuation, of application Ser. No. 363,521, filed May 24, 1973 now abandoned.

BACKGROUND OF THE INVENTION

1. Field of the Invention

This invention relates to a catalyst composition having a long catalyst life and adapted to be used for the gas phase catalytic oxidation of $\alpha,\beta$-unsaturated olefinic hydrocarbons (alkenes $C_nH_{2n}$).

2. Description of the Prior Art

In the industrial practice of rections using catalysts, a primary problem to be solved is generally the problem of improving the activity and selectivity of the catalysts to be used. From an industrial viewpoint, it is important to maintain the catalyst life for a long time while maintaining the expected activity and selectivity of the catalyst. The term "catalyst life" referred herein means the time period beginning with the time at which the intended oxidation reaction begins and ending at the time at which the amount of the intended product is reduced below the economical level due to degradation of the activity of the catalyst during the practice of the gas phase catalytic oxidation.

In preparing the $\alpha,\alpha$-unsaturated aldehydes by oxidation of $\alpha,\beta$-unsaturated hydrocarbons, it is well known in the art that oxidation catalysts comprising molybdenum oxide are effective, and various kinds of catalysts of this type have heretofore been used. As a result of our research, however, we have found that these catalysts have a fatal defect, namely, a short catalyst life, and they cannot be used effectively on an industrial basis.

As a reason for this deficiency, it is stated at page 395 of "Practical Catalysts Classified by Reactions" (published by Kagaku Kogyosha) that "in catalysts of the molybdenum series degradation is brought about by scattering of molybdenum".

An effective solution of this problem has not heretofore been attained in the art. In this connection, Japanese patent publication No. 1848/66 proposes a process in which salts of catalyst components are fed into the reactor during the progress of the reaction, together with the starting material, to compensate for the amounts of the catalyst components consumed during the reaction. This technique is based on the assumption that the degradation of the catalyst activity is brought about by loss of the catalyst surface.

However, in such a method the reaction apparatus and operational procedure are complicated, which results in an increase in the manufacturing cost. Accordingly, such a process is not industrially convenient and it does not provide a fundamental improvement of the catalyst, per se, such as is intended in this invention.

With a view to preparing acrolein, we conducted experiments involving the reaction of oxidizing propylene with molecular oxygen using catalysts comprising an oxide of a metal, such as molybdenum, bismuth, iron or arsenic, supported on silica as a carrier. We examined the reaction with respect to the important factors of propylene conversion and acrolein selectivity, in relation to the passage of reaction time. In these experiments propylene was passed once through a catalyst layer within recycling propylene.

As a result, it was found that when the reaction is carried out at a temperature usually adopted in the art for this reaction, namely, at 370° – 400° C, the acrolein selectivity tends to decrease gradually even within a reaction period of not more than 1000 hours. When the reaction is carried out at a lower temperature in order to prevent the loss or degradation of the metal oxide, the conversion of propylene is reduced and the yield of acrolein and the output of acrolein per unit time and per unit weight of the catalyst is also reduced.

From the results of these experiments, it was confirmed that the tendency of degradation of the catalyst activity is conspicuous, especially in catalyst compositions comprising molybdenum oxide as one catalytic component.

Among the catalyst compositions for oxidation of $\alpha,\beta$-unsaturated hydrocarbons which have heretofore been proposed, some give very good results as regards the conversion of the starting hydrocarbon and the selectivity of the intended product. However, they are generally catalysts containing a high content of metal oxides such as 80% by weight, based on the carrier. These catalysts are very expensive and are disadvantageous to use industrially unless their catalyst life is extremely long.

We have noted that in the high temperature reaction there occurs an undesired phenomenon, namely, that molybdenum oxide in the catalyst composition is scattered and consumed, which results in a reduction of the catalyst activity. We have carried out extensive research with a view to developing catalysts capable of given a high conversion of the starting material and a high selectivity of the intended product in order to meet fully industrial demands, employing as low a reaction temperature as possible, using catalysts having a relatively low metal content, based on the carrier, and also having a very long catalyst life.

We have discovered that the configuration, structure and physical properties of silica used as a catalyst carrier are very important for maintaining the desired physical condition of the catalyst and exert a great influence on the catalytic activity of the metal oxide supported thereon, especially the catalyst life.

SUMMARY OF THE INVENTION

According to this invention there is provided a process for preparing $\alpha,\beta$-unsaturated carbonyl compounds by oxidizing $\alpha,\beta$-unsaturated hydrocarbons with molecular oxygen, employing a catalyst composition obtained by supporting at least two metal compounds, at least one of which contains molybdenum, on silica having a specific surface area of at least 250 m²/g, preferably 300 to 700 m²/g, as a carrier. The catalyst composition has a specific surface area of 100 to 250 m²/g, preferably 150 to 200 m²/g.

Silica has heretofore been used generally as a carrier for the catalyst for the reaction of oxidizing $\beta,\alpha$-unsaturated olefins. According to the prior art as is disclosed, for instance, in "Lectures on Catalyst Engineering, Vol. 10, Catalyst Handbook" published by Chijin Shokan on Feb. 25, 1967, it has heretofore been considered to be essential that the surface area of the silica employed as a carrier should be as low as possible, not exceeding 100 m²/g, in order to inhibit occurrence of side reactions.

Accordingly, silica carriers usually employed in catalysts of this type are prepared by calcining the starting silica having a specific surface area of from 10 to several m²/g at a temperature exceeding 500° C or treating it with an alkali or other chemical liquor. None of the prior art recommends the use of silica having a specific surface area of at least 250 m²/g, such as is employed in this invention.

Furthermore, in this invention, in preparing catalyst compositions employing such silica carrier, metal oxides containing molybdenum are supported on the silica carrier so that the resulting catalyst composition has a specific surface area of 100 to 250 m²/g. The use of a catalyst composition meeting such conditions makes it possible to achieve the advantageous effects of high activity and selectivity, at relatively low reaction temperatures and with long catalyst life.

As regards the specific surface area of the catalyst composition, the above-mentioned "Practical Catalysts Classified by Reactions" states that catalysts having a specific surface area of 1 to 250 m²/g can be used but it also teaches that because a combustion reaction readily occurs as the surface area is increased in this range, it is important to employ a catalyst having as small a specific surface area as possible to avoid this problem. This statement, therefore, is very ambiguous and does not teach effective range of the specific surface area of the catalyst employed in this invention.

In connection with the relationship between the carrier and the final catalyst composition, this invention specifies that the final catalyst composition should have a specific surface are of at least 100 m²/g. This lower limit is essential in order to maintain high catalyst activity in a relatively low reaction temperature and to prolong the catalyst life. Thus, this invention provides a technical concept which is unobvious and is unexpectedly superior to the conventional techniques in the art.

The silica carrier employed in this invention can be in either the sol form or the gel form, and the process of preparing same is not critical. For example, a silica carrier having a specific surface area of at least 250 m²/g, preferably 300 to 700 m²/g, which is prepared by treating sodium silicate with a mineral acid, washing the resulting product with water and drying it, can be effectively used in this invention.

Accordingly, silica gels, usually used as desiccants, can be used as is without being calcined or treated with an alkali or the like.

As metal oxides effective as the active catalyst components in this invention, these are not critical, except that the compounds or mixtures employed must contain as one component an oxide of molybdenum and must also contain at least one additional metal oxide component comprising a metal other than molybdenum. The molybdenum oxide is not necessarily the principal component in a quantitative sense. It is sufficient if the molybdenum oxide is contained, as one catalytic component for the oxidation reaction, in an amount which is sufficient to exert the desired catalytic activity in accordance with the prior art techniques of preparing $\alpha,\beta$-unsaturated carbonyl compounds from $\alpha,\beta$-unsaturated olefins. As a result of our studies, it has been found that the amount of the molybdenum oxide for effectively attaining the above object is at least about 25% by weight, based on the total metal oxides in the catalyst composition. It is recommended to employ bismuth as a second metal component to be used in combination with molybdenum. But other metals such as iron, arsenic, antimony, sulfur, phosphorus, tungsten, nickel, cobalt, sodium and potassium can also be used, singly or in combination, as a metal component to be used in conjunction with molybdenum. The amount of the other metal oxide or oxides is at least 25% by weight, based on the total metal oxides in the catalyst composition.

The additional metal oxide or oxides employed are not critical and any metal oxide that is effective as a catalytic component for an oxidation reaction of $\alpha,\beta$-olefins, in combination with molybdenum oxide, can be used in the catalyst composition of this invention.

These catalyst components are generally made present in the form of their oxides by heating the corresponding nitrates, hydrochlorides, sulfates or ammonium salts in air. Thus, the catalyst composition of this invention can be prepared by spraying aqueous solutions of these salts on the silica carrier or by immersing the silica carrier in such aqueous solutions to thereby disperse and apply these salts uniformly on the carrier and then drying the thus-treated carrier. The thus-treated carrier can be molded into various shapes, but this is optional. The amounts of the metal oxides supported on the carrier have a very close relation to the specific surface area of the carrier and the specific surface area of the resulting catalyst composition. The amounts of the metal oxides to be supported on the carrier should be chosen appropriately depending on the specific surface area of the silica carrier actually used, so that the resulting catalyst composition has a specific surface area of 100 to 250 m²/g.

However, even if the resulting catalyst composition has a specific surface area within the range specified in this invention, if the total amount of the metal oxides in the catalyst is too high, in the oxidation of propylene there is observed an undesirable tendency that the acrylic acid selectivity increases while the yield of acrolein decreases. Therefore, in this invention the total amount of metal oxides supported on the silica carrier is within the range of from 25 to 40% by weight, based on the silica carrier.

When a catalyst composition, in which the silica carrier used has a specific surface area of less than 250 m²/g and in which the catalyst composition has a specific surface area outside the range of from 100 to 250 m²/g, is used for the oxidation reaction, although it sometimes exhibits a relatively high activity at the relatively high reaction temperature conventionally adopted, i.e., 360° – 380° C, at the initiation of the reaction, its catalyst life is relatively short and when the reaction is continued for about 1000 hours, the activity is generally degraded. Further, when the oxidation is carried out in the presence of such a catalyst composition, with the further measure of reducing the reaction temperature below 350° C so as to prolong the catalyst life, the desired initial activity cannot be obtained.

In contrast, when there is employed a catalyst composition containing a carrier having a specific surface area within the range of this invention and the catalyst composition has a specific surface area within the range specified in this invention, a very high initial catalytic activity can be attained even at a relatively low reaction temperature of 310° – 340° C. It is possible, therefore, to conduct the reaction at relatively lower temperatures and to maintain the catalyst life for more than 6000 hours while maintaining the initial high catalytic activity.

Even when the carrier employed has a preferred specific surface area of 300 to 700 m²/g, if the specific surface area of the resulting final catalyst composition exceeds 250 m²/g, combustion of the starting olefin is likely to occur and the selectivity of the desired product decreases. Therefore, use of such a catalyst composition is not acceptable in this invention.

In this invention, metal oxides are supported on a silica carrier having a much greater specific surface area than conventional silica carriers. Hence, the amounts of the supported metal oxides supported thereon are decreased. This reduces the catalyst manufacturing cost. Moreover, not only at lower reaction temperatures, but also at higher reaction temperatures such as 360° C or more, the conversion of the starting material and the selectivity of the desired product can be maintained for a very long period of time at high levels comparable or superior to those attained in the conventional techniques.

In practicing the oxidation reaction of $\alpha,\beta$-unsaturated olefins, a danger of explosion or propagation of flame is always present and hence, it is an important requirement to minimize the occurrence of such dangerous phenomenon. In many cases, this phenomenon is caused to occur by improper selection of reaction conditions such as the reaction temperature, the reaction pressure, the mole ratio of the charged gases and the like.

We have studied these factors and have confirmed ranges of these factors assuring safe operation. More specifically, even in the case of the gas composition presently considered to be the safest, i.e., a composition comprising 1 mole of propylene, 8 moles of air and 6 moles of steam, at 300° C under pressure, this condition is very close to the flame-propagation range. In a gas composition comprising 1 mole of propylene, 15 moles of air and 1 mole of steam, the condition is very dangerous and is within the explosion range. However, when the reaction is carried out using the catalyst composition of this invention, it is possible to effect the reaction at a lower temperature while maintaining high activity for a long time. It has been confirmed that the safe range of the ratio of air to other materials in the starting gas charge can be broadened and the reaction can still be carried out very safely. This is one of the important advantages of this invention.

The catalyst of this invention can be used for the preparation of $\alpha,\beta$-unsaturated aldehyde compounds by catalytically oxidizing $\alpha,\beta$-olefins having from 3 to 4 carbon atoms with molecular oxygen, especially preferably for preparing from propylene or isobutylene the corresponding unsaturated aldehyde compound. The oxidation reaction can be carried out employing conventional procedures. More specifically, reactors of the fluidized bed-type, fixed bed-type and moving bed-type can be employed. A gaseous mixture comprising an olefin, oxygen, and, optionally, nitrogen and steam, in which the olefin:oxygen mole ratio is, for instance, from 1:0.5 to 1:2, or in which water is present in an amount of 2 to 8 moles per mole of the olefin, is preheated at 200° – 300° C and then is passed through the catalyst layer at a reaction temperature of 300° to 500° C, preferably 310° to 340° C. It is preferred that the contact time is 0.1 to 10 seconds, especially 0.5 to 5 seconds.

Further details of the technical content and effects of this invention will be described by reference to the following illustrative examples, comparative examples and the accompanying drawings.

Figure 1:
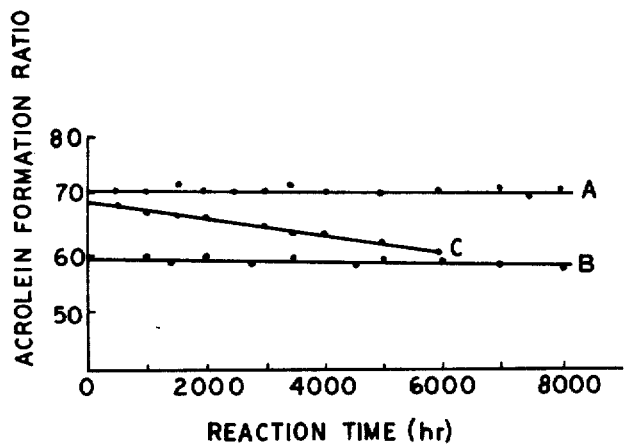
FIG. 1 is a graph of acrolein formation ratio versus reaction time for the catalysts of Example 1 and Comparative Example 1.

In the examples, the values of propylene conversion, acrolein formation ratio and acrolein selectivity are calculated according to the following definitions:

$$\text{Propylene conversion (mole \%)} = \frac{\text{moles of converted propylene}}{\text{moles of charged propylene}} \times 100$$

$$\text{Acrolein formation ratio (mole \%)} = \frac{\text{moles of formed acrolein}}{\text{moles of charged propylene}} \times 100$$

$$\text{Acrolein selectivity (mole \%)} = \frac{\text{moles of formed acrolein}}{\text{moles of converted propylene}} \times 100$$

EXAMPLE 1

14.95 Parts by weight of ammonium molybdate [$(NH_4)_6Mo_7O_{24}.4H_2O$] was dissolved in 50 parts by volume of water with heating.

Separately, 21.35 parts by weight of ferric nitrate [$Fe(NO_3)_3.9H_2O$], 1.88 parts by weight of pyroarsenic acid, 15.39 parts of bismuth nitrate [$Bi(NO_3)_3.5H_2O$] and 0.26 part by weight of potassium nitrate were dissolved with heating in a second solution acidified with nitric acid, and the above ammonium molybdate solution was added to the thus-formed second solution. Then, 50 parts of silica gel having a specific surface area of 660 m$^2$/g and pulverized to have a size smaller than 150 mesh was added to the mixed solution, and the solution was then concentrated. The silica gel thus treated was dried sufficiently in air at 120° C and the resulting catalyst composition was heated in air at 350° C for 2 hours to decompose the salts to form the metal oxides, then pulverized and molded into cylindrical pellets having a diameter of 5 mm and a length of 5 mm by employing a pelleting machine. The thus-molded catalyst composition was calcined at 540° C for 4 hours prior to use. The resulting catalyst composition had a specific surface area of 175 m$^2$/g as measured by the BET method (nitrogen-adsorbing method), and the metal oxide concentration thereof was 35% by weight.

60 cc of the thus-obtained catalyst composition was packed in a U-shaped reaction tube made of stainless steel, and a gaseous mixture comprising 6 mole % of propylene and 42.8 mole % of air, the balance being steam, was passed through the reaction vessel so that the contact time was 2.4 seconds.

This procedure was carried out at different reaction temperatures. The relationship between the activity of the catalyst and the reaction temperature is as shown in Table 1.

Comparative Example 1

The preparation of the catalyst and the oxidation of propylene were carried out in the same manner as in Example 1 except that a silica carrier having a specific surface area of 150 m$^2$/g was employed. The catalyst activity and the selectivity of the intended product were examined and the results shown in Table 1 were obtained. The catalyst composition obtained in this Comparative Example had a specific surface area of 80 m$^2$/g.

Table 1

|  | Example 1 | | | Comparative Example 1 | | |
| --- | --- | --- | --- | --- | --- | --- |
| Specific Surface Area of Carrier Used | 660 m²/g | | | 150 m²/g | | |
| Specific Surface Area of Catalyst | 175 m²/g | | | 80 m²/g | | |
| Reaction Temperature (° C) | Propylene Conversion | Acrolein Formation Ratio | Acrolein Selectivity | Propylene Conversion | Acrolein Formation Ratio | Acrolein Selectivity |
| 400 | 97.1 | 61.2 | 63.0 | 93.3 | 62.0 | 66.4 |
| 385 | 96.9 | 63.6 | 65.6 | 94.5 | 67.3 | 71.0 |
| 370 | 94.4 | 68.1 | 72.2 | 87.1 | 63.7 | 73.1 |
| 360 | 93.0 | 68.6 | 74.5 | — | — | — |
| 355 | 92.2 | 69.5 | 75.4 | 82.1 | 63.1 | 76.8 |
| 340 | 87.5 | 71.2 | 81.2 | 75.4 | 59.0 | 78.2 |
| 325 | 82.4 | 68.0 | 82.6 | 68.3 | 56.0 | 82.1 |
| 310 | 67.5 | 59.6 | 88.4 | 58.4 | 47.9 | 82.1 |

From the results shown in Table 1, it is seen that the acrolein formation ratio is influenced by the specific surface area of the catalyst and the reaction temperature. Further, as illustrated in FIG. 1, at the reaction temperature of 340° C, both the catalyst of Example 1 (A in FIG. 1) and the catalyst of Comparative Example 1 (B in FIG. 1) exhibit a long catalyst life, but the catalyst of Comparative Example 1 has a low activity. At the reaction temperature of 360° C., the catalyst of Example 1 (C in FIG. 1) exhibits a high activity with an acceptably long catalyst life.

EXAMPLE 2

A catalyst was prepared in the same manner as described in Example 1 except that a silica carrier having a specific surface area of 285 m²/g was employed. The resulting catalyst had a specific surface area of 137 m²/g. When the activity of this catalyst composition for oxidizing propylene was examined, it was found that the propylene conversion was 90.6% at 355° C and 82.2% at 340° C and the acrolein formation ratio was 66.6% at 355° C and 66.1% at 340° C. Thus, the reactivity of the catalyst was hardly changed by these different reaction temperatures. In the case of the catalyst of this Example, the initial activity was high, and the activity was excellent especially at the lower reaction temperature and the catalyst life was long even at the higher reaction temperature.

EXAMPLE 3 AND COMPARATIVE EXAMPLE 2

The catalyst preparation procedures described in Example 1 were repeated except for employing silica having a specific surface area of 480 m²/g to obtain a catalyst having a specific surface area of 258 m²/g (calcined at 400° C for 4 hours) (Comparative Example 2) and a catalyst having a specific surface area of 172 m²/g (calcined at 540° C for 4 hours) (Invention Examle 3). Using these two catalysts having the same composition, but differing in their specific surface area, oxidation was carried out in the same manner as in Example 1. The results shown in Table 2 were obtained.

Table 2

| Specific Surface Area of Catalyst | Example 3 | | Comparative Example 2 | |
| --- | --- | --- | --- | --- |
| | 172 m²/g | | 258 m²/g | |
| Reaction Temperature (° C) | Propylene Conversion | Acrolein Formation Ratio | Propylene Conversion | Acrolein Formation Ratio |
| 385 | 89.7 | 62.4 | 55.1 | 32.1 |
| 355 | 85.2 | 67.7 | * | * |
| 340 | 78.2 | 64.6 | * | * |

* Since the catalyst of Comparative Example 2 did not exhibit an industrially acceptable activity at 385° C, the reaction at lower temperatures, i.e., 355° C and 340° C was not conducted in the case of this catalyst.

From the results shown in Table 2, it is seen that the catalyst having a specific surface area of 258 m²/g has an insufficient activity for preparing acrolein economically.

Figure 2:
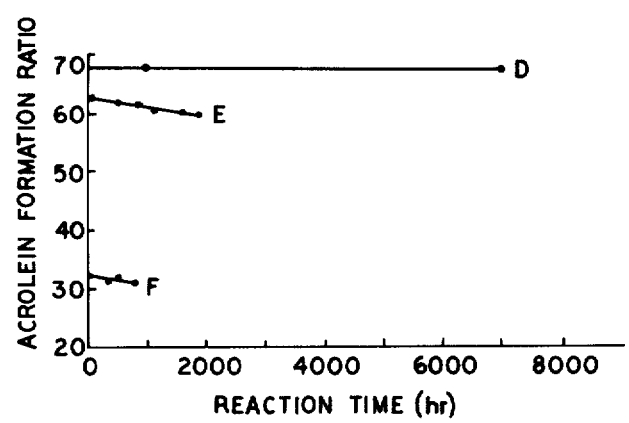
FIG. 2 is a graph of acrolein formation ratio versus reaction time for the catalysts of Example 3 and Comparative Example 2.

Further, as is illustrated in FIG. 2, the catalyst of this Example 3 (D and E in FIG. 2) had a very long life at a temperature at which it exhibited a sufficient activity (355° C), and at 385° C it had an industrially sufficient life.

In contrast, the catalyst of the Comparative Example 2 (F in FIG. 2) had an unacceptably short catalyst even at a temperature at which it did not exhibit an industrially significant activity (385° C).

EXAMPLE 4 AND COMPARATIVE EXAMPLE 3

23.78 Parts of ammonium molybdate were dissolved in 80 parts by volume of water. Separately, 34.03 parts by weight of ferric nitrate, 0.46 of potassium nitrate, 24.50 parts of bismuth nitrate and 1.29 parts by volume of 85% phosphoric acid were dissolved in 22.5 parts by volume of water. Both the solutions were mixed, and 50 parts by weight of silica having a specific surface area of 600 m²/g was added to the mixed solution, following by concentration under heating and drying at 120° C. The resulting powder was heated at 350° C in air to decompose the salts, and the molding and calcination were carried out in the same manner as in Example 1.

The metal oxide concentration in the resulting catalyst was 45% by weight. Two catalysts having a specific area of 255 m²/g and a specific surface area of 129 m²/g were obtained, the reason for which is still unknown. The activities of these catalysts were examined in the same manner as in Example 1 and the results shown in Table 3 were obtained. The calcination was carried out at 540° C for 4 hours in both of the above two catalysts.

Table 3

| | Example 4 | | Comparative Example 3 | |
|---|---|---|---|---|
| Specific Surface Area of Catalyst | 129 m²/g | | 255 m²/g | |
| Reaction Temperature (° C) | Propylene Conversion | Acrolein Formation Ratio | Propylene Conversion | Acrolein Formation Ratio |
| 385 | 93.1 | 64.5 | 79.5 | 55.0 |
| 355 | 85.9 | 67.0 | 75.0 | 50.4 |
| 340 | 78.9 | 60.8 | 68.0 | 48.2 |

With respect to each catalyst, the catalyst life was examined at the temperature at which the highest acrolein formation ratio among the data shown in the above Table was attained. In the case of the catalyst of Example 4 at 355° C, after the reaction had been continued for about 5000 hours, the decrease of the acrolein formation ratio was only 4.0%.

Comparative Example 4

The procedure of Example 4 were repeated except that the amounts of metal salts used were doubled. The metal oxide content in the resulting catalyst was 65% by weight and the specific surface area of the catalyst was 65 m²/g. The activity of the thus-formed catalyst was examined in the same manner as in Example 1 and it was found that the propylene conversion was 70.4% at 370° C and 60.4% at 355° C and the acrolein formation ratio was 44.1% at 370° C and 41.4% at 355° C. Thus, it is apparent that the catalyst obtained in this comparative example was must inferior to the catalyst of Example 4 with respect to its activity of converting propylene to acrolein.

EXAMPLE 5 AND COMPARATIVE EXAMPLE 5

15.5 Parts of weight of ammonium molybdate was dissolved under heat in 53 parts by volume of water. Separately, 22.18 parts by weight of ferric nitrate, 2.13 parts by weight of cobalt nitrate [Co(CO₃)₂.6H₂O], 15.94 parts of bismuth nitrate and 0.022 part by weight of potassium nitrate were dissolved with heating in a solution acidified with nitric acid, and 0.84 part by volume of 85% phosphoric acid was added thereto. Both the solutions were combined.

Then, 50 parts by volume of silica having a specific surface area of 600 m²/g was added to the mixed solution, followed by concentration under heating. Post treatments were carried out in the same manner as in Example 1 to obtain a catalyst composition having a metal oxide concentration of 35% by weight and a specific surface area of 160 m²/g.

For comparison, a catalyst composition was prepared in the same manner as above except that silica having a specific surface area of 200 m²/g was employed. The resulting catalyst had a specific surface area of 85 m²/g.

The oxidation of propylene was carried out in the same manner as in Example 1, using these catalysts, and the results shown in Table 4 were obtained. The catalyst life of Example 5 was examined under the conditions that gave the maximum acrolein formation ratio in the case of the catalyst of this example. As a result, it was found that even after the reaction had been continued for 5000 hours at 340° C, no decrease of the reactivity was observed.

Table 4

| | Example 5 | | Comparative Example 5 | |
|---|---|---|---|---|
| Specific Surface Area of Silica Carrier | 600 m²/g | | 200 m²/g | |
| Specific Surface Area of Catalyst | 160 m²/g | | 85 m²/g | |
| Reaction Temperature (° C) | Propylene Conversion | Acrolein Formation Ratio | Propylene Conversion | Acrolein Formation Ratio |
| 400 | 90.3 | 58.2 | 92.1 | 60.2 |
| 385 | 89.8 | 59.0 | 90.1 | 67.5 |
| 370 | 87.5 | 60.3 | 85.4 | 62.6 |
| 355 | 87.1 | 64.8 | 81.8 | 59.4 |
| 340 | 81.7 | 66.0 | 72.1 | 51.0 |
| 325 | 73.9 | 60.6 | 63.3 | 48.0 |

EXAMPLE 6 AND COMPARATIVE EXAMPLE 6

16.04 Parts by weight of ammonium molybdate was dissolved with heating in 53 parts by volume of water. Separately, 22.94 parts by weight of ferric nitrate, 16.53 parts by weight of bismuth nitrate, 0.39 part by weight of potassium nitrate and 0.41 part by weight of boric acid ($H_3BO_3$) were dissolved into 15 parts by volume of an aqueous solution acidified with nitric acid. Both the solutions were mixed with heating, and a silica carrier having a specific surface area of 600 m²/g was added in an amount of 48 parts by weight to the mixed solution.

Post treatments were conducted in the same manner as in Example 1 to obtain a catalyst composition having a specific surface area of 234 m²/g and a metal oxide content of 35% by weight.

The above procedures were repeated in the same manner as above, except that a silica carrier having a specific surface area of 150 m²/g was employed. The resulting catalyst had a specific surface area of 80 m²/g. This catalyst was designated as the catalyst of Comparative Example 6.

With respect to each catalyst, the activity was determined according to the method described in Example 1 and the results shown in Table 5 were obtained.

As a result of examination of the change in the catalyst activity with the passage of time, at the reaction temperature at which the maximum acrolein formation ratio was attained, it was found in the case of the catalyst of Example 6 that after the reaction had been continued for 4000 hours at 340° C, the catalyst activity was not reduced at all.

to 200 m²/g, and the reaction temperature is in the range of from about 310° to about 340° C.

Table 5

|  | Example 6 | | Comparative Example 6 | |
| --- | --- | --- | --- | --- |
| Specific Surface Area of Silica Carrier | 600 m²/g | | 150 m²/g | |
| Specific Surface Area of Catalyst | 234 m²/g | | 80 m²/g | |
| Reaction Temperature (° C) | Propylene Conversion | Acrolein Formation Ratio | Propylene Conversion | Acrolein Formation Ratio |
| 400 | 90.6 | 55.3 | 93.3 | 59.9 |
| 370 | 87.7 | 58.9 | 90.4 | 68.2 |
| 355 | 85.8 | 64.2 | 86.2 | 63.3 |
| 340 | 84.4 | 69.8 | 81.4 | 59.6 |
| 325 | 76.0 | 64.1 | 70.1 | 54.0 |

The embodiments of the invention in which an exclusive property or privilege is claimed are defined as follows:

1. In a process for preparing an α,β-unsaturated aldehyde by the gas phase catalytic oxidation of the corresponding α,β-unsaturated olefinic hydrocarbon, which comprises contacting a gas phase mixture of said olefinic hydrocarbon and molecular oxygen, with a catalyst composition consisting essentially of a carrier having deposited thereon a mixture of at least two metal oxides, at least one of which is molybdenum oxide in an amount of at least about 25% by weight, based on the total metal oxides, and the other metal oxide or metal oxides also being present in an amount of at least 25% by weight, based on the total metal oxides, the improvement which comprises; the carrier of said catalyst composition consists of silica having a specific surface area of 250 m²/g up to 700 m²/g, the catalyst composition has a specific surface area in the range of from 150 m²/g to 200 m²/g, and the reaction temperature is in the range of from about 310° to about 340° C.

2. A process according to claim 1, in which the silica has a specific surface area in the range of from 300 to 700 m²/g.

3. A process according to claim 1, in which said other metal oxides contain bismuth oxide.

4. A process according to claim 1, in which the other metal oxides are selected from the group consisting of oxides of iron, arsenic, antimony, sulfur, phosphorus, tungsten, nickel, cobalt, sodium, potassium and mixtures thereof.

5. A process according to claim 1, in which the mole ratio of olefinic hydrocarbon : oxygen is in the range of 1 : 0.5 to 1 : 2.

6. A process according to claim 5, in which the gas phase contains from 2 to 8 moles of steam per mole of olefinic hydrocarbon and the molecular oxygen is supplied in the form of air.

7. A process according to claim 1, in which the olefinic hydrocarbon is propylene or isobutylene.

* * * * *